US012808859B2

(12) United States Patent
Park et al.

(10) Patent No.: US 12,808,859 B2
(45) Date of Patent: Nov. 24, 2026

(54) METHOD AND DEVICE FOR MEASURING A SIGNAL OF A LIVING CELL

(71) Applicant: SAMSUNG ELECTRONICS CO., LTD., Suwon-si (KR)

(72) Inventors: Kitae Park, Suwon-si (KR); Chisung Bae, Suwon-si (KR); Jaechun Lee, Suwon-si (KR); Hyeokki Hong, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 739 days.

(21) Appl. No.: 18/187,958

(22) Filed: Mar. 22, 2023

(65) Prior Publication Data

US 2024/0077468 A1 Mar. 7, 2024

(30) Foreign Application Priority Data

Sep. 5, 2022 (KR) ........................ 10-2022-0112012

(51) Int. Cl.
*G01N 33/50* (2006.01)
*C12M 1/34* (2006.01)
*G01N 27/327* (2006.01)
*G01N 33/483* (2006.01)

(52) U.S. Cl.
CPC ......... *G01N 33/5005* (2013.01); *C12M 41/46* (2013.01); *G01N 27/327* (2013.01); *G01N 33/4836* (2013.01)

(58) Field of Classification Search
None
See application file for complete search history.

(56) References Cited

U.S. PATENT DOCUMENTS 6,032,062 A * 2/2000 Nisch ........................ A61N 1/05 607/148
8,352,045 B2 * 1/2013 Joucla ...................... A61N 1/05 607/116
2003/0113832 A1 * 6/2003 Lauf ........................ C12Q 1/02 435/287.1
2005/0142033 A1 * 6/2005 Glezer .................. B01L 3/5085 422/400
2005/0196776 A1 * 9/2005 Yang .................. G01N 27/3277 435/6.12

(Continued)

FOREIGN PATENT DOCUMENTS

CN 101614729 A 12/2009
CN 113466110 A 10/2021
JP 2022-500021 A 1/2022

*Primary Examiner* — Henry H Nguyen
(74) *Attorney, Agent, or Firm* — NSIP Law

(57) ABSTRACT

A method and device for measuring living cells are provided. A device includes a culture vessel in which a living cell is cultured; and a multi-electrode array (MEA) including first electrodes arranged with a pattern and configured to conductively receive an electrical signal generated by the living cell and conductively transmit an electrical signal to the living cell through the first electrodes, wherein the culture vessel is mateable with the MEA, and configured to, when mated with the MEA, conductively transmit an electrical signal generated by the living cell to the first electrodes or conductively transmit an electrical signal to the living cell via the first electrodes through a surface mated with the MEA.

7 Claims, 9 Drawing Sheets

(56) References Cited

U.S. PATENT DOCUMENTS

| | | | | |
|---|---|---|---|---|
| 2009/0322309 | A1 | 12/2009 | Zhu et al. | |
| 2014/0087213 | A1* | 3/2014 | Park | H01M 8/0247 429/2 |
| 2019/0011424 | A1* | 1/2019 | McRuer | G01N 33/48721 |
| 2019/0049433 | A1* | 2/2019 | Ehret | A61B 5/271 |
| 2019/0391127 | A1 | 12/2019 | Braeken et al. | |
| 2021/0069697 | A1* | 3/2021 | Azizgolshani | C12M 41/08 |
| 2021/0198613 | A1* | 7/2021 | Curley | G01N 33/5014 |
| 2021/0310979 | A1* | 10/2021 | Gandolfo | G01N 33/4836 |
| 2021/0313987 | A1* | 10/2021 | Faldu | A61N 1/05 |

* cited by examiner

METHOD AND DEVICE FOR MEASURING A SIGNAL OF A LIVING CELL

CROSS-REFERENCE TO RELATED APPLICATIONS

This application claims the benefit under 35 USC § 119(a) of Korean Patent Application No. 10-2022-0112012, filed on Sep. 5, 2022, in the Korean Intellectual Property Office, the entire disclosure of which is incorporated herein by reference for all purposes.

BACKGROUND

1. Field

The following description relates to a method and device for measuring an electrical signal from a living cell.

2. Description of Related Art

Multi-electrode array (MEA) systems are used for measuring electrical activations of living cells and natural neural networks. In an MEA system, living cells may be cultured on an MEA and the MEA system may measure electrical activations generated by the living cells by measuring electrical signals from the living cells. With such measuring of electrical signals generated by living cells, it may be possible to dynamically analyze connection states of the cells and connection strengths between the cells.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a device includes: a culture vessel in which a living cell is cultured; and a multi-electrode array (MEA) including first electrodes arranged with a pattern and configured to conductively receive an electrical signal generated by the living cell and conductively transmit an electrical signal to the living cell through the first electrodes, wherein the culture vessel is mateable with the MEA, and configured to, when mated with the MEA, conductively transmit an electrical signal generated by the living cell to the first electrodes or conductively transmit an electrical signal to the living cell via the first electrodes through a surface mated with the MEA.

The culture vessel may include a conductive material formed on the bottom and the conductive material may include portions arranged in the pattern of the first electrodes.

The bottom of the culture vessel may include through-holes containing the respective portions of the conductive material.

The first electrodes may be configured such that when the MEA is mated with the culture vessel the first electrodes are inserted into the respective portions of the conductive material.

The first electrodes being inserted into the portions of the conductive material may include ends of the first electrodes deforming or penetrating the portions of the conductive material.

The culture vessel may include a porous membrane on the bottom.

The culture vessel may include second electrodes vertically penetrating the bottom and arranged with the pattern.

The MEA may include: an integrated circuit; and a passivation layer formed on one side of the integrated circuit, and wherein the first electrodes may be connected to the integrated circuit through the passivation layer.

In another general aspect, a culture vessel includes: a bottom including an interior surface to which a living cell is applied and cultured; and one or more sidewalls adjoining the bottom such that the bottom and the one or more sidewalls define a receptacle of the culture vessel, wherein the bottom is configured to be electromechanically separated from and mateable with a multi-electrode array (MEA) including first electrodes, and wherein the bottom is configured to, when mated to the MEA, conductively transmit an electrical signal from the living cell to the first electrodes or conductively transmit an electrical signal to the living cell via the first electrodes.

The bottom may include through-holes containing respective portions of a conductive material, wherein the through-holes and portions are arranged in a same pattern as the first electrodes.

The bottom may further include a porous membrane.

The bottom may include second electrodes vertically penetrating the bottom and arranged in the pattern.

In another general aspect, a measurement method includes: transmitting a first electrical signal to a living cell via first electrodes of a multi-electrode array (MEA) while a culture vessel in which the living cell is being cultured is physically and electrically coupled with the MEA; and receiving a second electrical signal generated by the living cell via the first electrodes, wherein the MEA includes the first electrodes, which are arranged in an array pattern, and wherein the MEA is configured to, when mated with the culture vessel, receive the second electrical signal generated by the living cell via the first electrodes and conductively transmit the first electrical signal to the living cell, and wherein the culture vessel and the MEA are configured to be conductively and physically mated and unmated, and configured to exchange the electrical signals first electrodes through a bottom of the MEA when the vulture vessel and the MEA are conductively and physically mated.

The culture vessel may include a conductive material, which may be formed on the surface attached to the MEA according to the array pattern.

When the MEA and the culture vessel are mated the first electrodes may be inserted into the conductive material by penetrating or deforming the conductive material.

The culture vessel may include a porous membrane on a bottom surface of the bottom or forming the bottom, and the porous membrane may be arranged to contact the MEA when the culture vessel and MEA are mated.

The culture vessel may include second electrodes vertically penetrating the bottom and configured with the array pattern.

The method may further include determining whether to continue culturing the living cell based on a strength of the second electrical signal.

The living cell may include a nerve cell, and the method may further include deriving information about a neural connection of the nerve cell based on the second electrical signal.

Other features and aspects will be apparent from the following detailed description, the drawings, and the claims.

Figure 1:
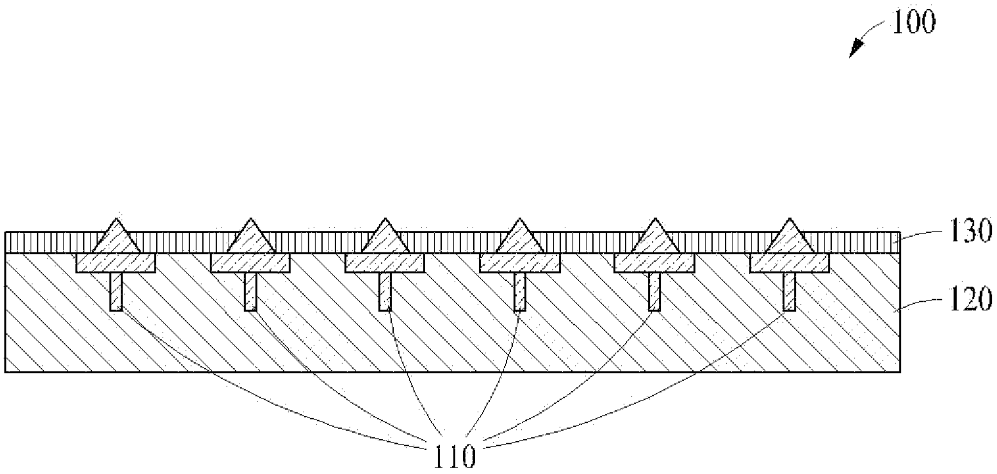
FIG. 1 illustrates an example of a multi-electrode array (MEA), according to one or more embodiments.

Throughout the drawings and the detailed description, unless otherwise described or provided, the same or like drawing reference numerals will be understood to refer to the same or like elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known after an understanding of the disclosure of this application may be omitted for increased clarity and conciseness.

The features described herein may be embodied in different forms and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

The terminology used herein is for describing various examples only and is not to be used to limit the disclosure. The articles "a," "an," and "the" are intended to include the plural forms as well, unless the context clearly indicates otherwise. As used herein, the term "and/or" includes any one and any combination of any two or more of the associated listed items. As non-limiting examples, terms "comprise" or "comprises," "include" or "includes," and "have" or "has" specify the presence of stated features, numbers, operations, members, elements, and/or combinations thereof, but do not preclude the presence or addition of one or more other features, numbers, operations, members, elements, and/or combinations thereof.

Throughout the specification, when a component or element is described as being "connected to," "coupled to," or "joined to" another component or element, it may be directly "connected to," "coupled to," or "joined to" the other component or element, or there may reasonably be one or more other components or elements intervening therebetween. When a component or element is described as being "directly connected to," "directly coupled to," or "directly joined to" another component or element, there can be no other elements intervening therebetween. Likewise, expressions, for example, "between" and "immediately between" and "adjacent to" and "immediately adjacent to" may also be construed as described in the foregoing.

Although terms such as "first," "second," and "third", orA, B, (a), (b), and the like may be used herein to describe various members, components, regions, layers, or sections, these members, components, regions, layers, or sections are not to be limited by these terms. Each of these terminologies is not used to define an essence, order, or sequence of corresponding members, components, regions, layers, or sections, for example, but used merely to distinguish the corresponding members, components, regions, layers, or sections from other members, components, regions, layers, or sections. Thus, a first member, component, region, layer, or section referred to in the examples described herein may also be referred to as a second member, component, region, layer, or section without departing from the teachings of the examples.

Unless otherwise defined, all terms, including technical and scientific terms, used herein have the same meaning as commonly understood by one of ordinary skill in the art to which this disclosure pertains and based on an understanding of the disclosure of the present application. Terms, such as those defined in commonly used dictionaries, are to be interpreted as having a meaning that is consistent with their meaning in the context of the relevant art and the disclosure of the present application and are not to be interpreted in an idealized or overly formal sense unless expressly so defined herein. The use of the term "may" herein with respect to an example or embodiment, e.g., as to what an example or embodiment may include or implement, means that at least one example or embodiment exists where such a feature is included or implemented, while all examples are not limited thereto.

FIGS. 1 through 9 illustrate various cross-sectional views of a multi-electrode array (MEA) 100, a culture vessel 200, and a cross-section of the MEA 100 and the culture vessel 200 coupled to each other. From a top-view of the MEA 100 and the culture vessel 200, such items may have various shapes, e.g., circular, rectangular, etc., and the top-view shape is not significant to the embodiments and examples described herein.

FIG. 1 illustrates an example of the MEA 100. The MEA 100 may include first electrodes 110, an integrated circuit 120, and a passivation layer 130.

The passivation layer 130 may be formed, for example, on one side of the integrated circuit 120. For example, the passivation layer 130 may be directly or indirectly coated on or applied to the upper side or surface of the integrated circuit 120. For example, the passivation layer 130 may prevent the integrated circuit 120 from corroding and prevent a surrounding environment from affecting the integrated circuit 120. The material of the passivation layer may depend on the chemical content of the surrounding environment and may be selected to be passive/inert with respect to the environment.

The first electrodes 110 may be formed with a pattern and on the same side of the integrated circuit 120 as the passivation layer 130. For example, as illustrated in FIG. 1, the first electrodes 110 may penetrate the coated passivation layer 130 such that one end of the first electrodes 110 are exposed. Another end of the first electrodes 110 may be connected to the integrated circuit 120. The first electrodes 110 may be arranged in a grid pattern, for example, with variously set intervals. The first electrodes 110 may be arranged with various other patterns, for example, hexagonal, rectilinear, diamond, irregular, etc. Of note will be a correspondence/matching of the pattern with patterns of other elements described below.

The first electrodes 110 are able to receive or transmit an electrical signal. For example, when the MEA 100 is coupled to the culture vessel 200, the first electrodes 110 may conductively receive or transmit the electrical signal through a conductive material 220 of the culture vessel 200.

The integrated circuit 120 may amplify the electrical signal(s) received from the first electrodes 110 and transmit the amplified electrical signal(s) to a signal processing device connected to the integrated circuit 120. For example, the integrated circuit may include a complementary metal-oxide-semiconductor (CMOS) based signal processing device (signal processor). The signal processing device may separately receive and process the electrical signals from the respective first electrodes 110.

For example, the CMOS-based MEA 100 may include the first electrodes 110 formed at high area-density on the one/upper side of the integrated circuit 120. That is, there may be a high number of first electrodes 110 per unit of area. A high density of first electrodes 110 enables the CMOS-based MEA 100 to resolve an electrical signal generated by neurons in the culture vessel 200 with a comparably high resolution or resolving power.

The integrated circuit 120 may include a multiplexer (MUX) and/or an amplifier. For example, the MUX may be connected to the first electrodes 110 and transmit electrical signals sensed by the first electrodes 110 to the signal processing device (e.g., a memory, a process, etc.) for processing thereby. The amplifier may be connected to each of the first electrodes 110 and amplify the electrical signals sensed/received by the first electrodes 110.

The CMOS-based MEA 100 may control the noise level of the received electrical signals using the amplifier. The first electrodes 110 and the amplifier included in the CMOS-based MEA 100 may be arranged to have a distance therebetween that is short enough to allow the CMOS-based MEA 100 to control the noise level of the electrical signals received thereby.

The signal processing device connected to the integrated circuit 120 may process the amplified (and possibly filtered) electrical signals and based on the electrical signals dynamically analyze connection states and/or connection strengths between living cells 300 in the culture vessel 200.

Figure 2:
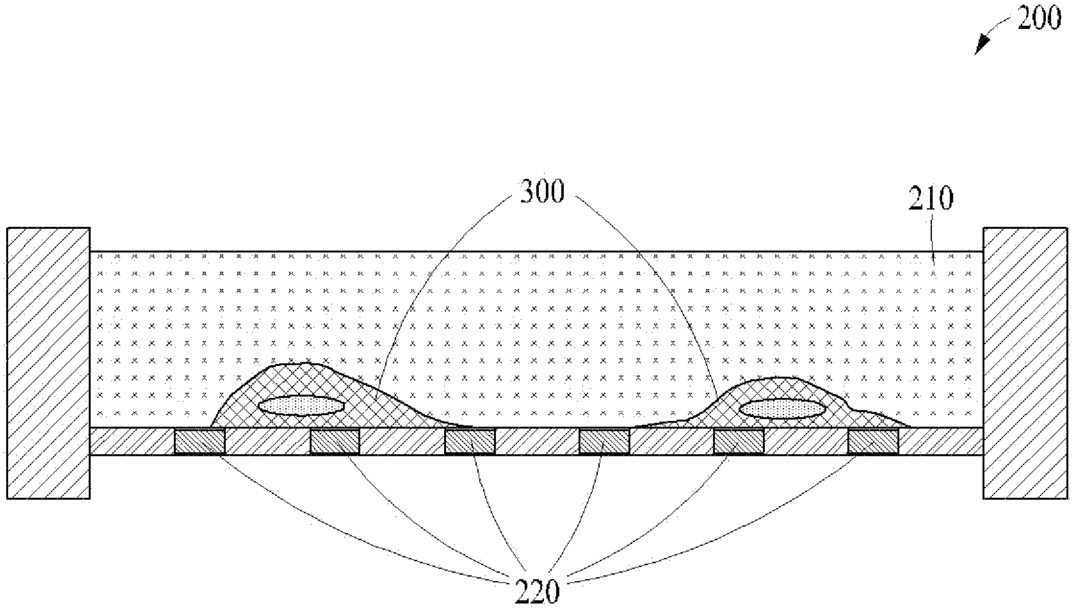
FIG. 2 illustrates an example of a culture vessel including a bottom on which a conductive material is patterned, according to one or more embodiments.

FIG. 2 illustrates an example of the culture vessel 200 including a lower surface on which the conductive material 220 is patterned. The culture vessel 200 may include a lower surface (a bottom) and sides (cylindrical embodiments have only a single side). The living cells 300 may be attached or applied to one side (e.g., an upper side) of the lower surface (bottom) and cultured.

For example, the side surfaces may extend from the one side of the lower surface and form an exterior/wall of the culture vessel 200. A culture medium 210 used to culture the living cells 300 may be provided to an inner space of the culture vessel 200 that is formed by the side surfaces and the lower surface (bottom). The side surface(s) and the bottom of the culture vessel 200 may form a receptacle for containing the living cells 300 and possibly culturing fluids or the like.

For example, the living cells 300 may include cells that may generate a measured electrical signal. The living cells 300 may be, for example, neural network tissue, organ tissue, and the like, but are not limited thereto. The living cells 300 may include cells cultured to generate a measurable electrical signal, including but not limited to human or animal cells. For example, artificially fabricated cells may be used, as well as hybrid cells, different types of cells at the same time, and so forth. Moreover, although description herein may refer to cells, any biological tissue may be measured.

The culture vessel 200 may be removably attached or coupled to an MEA (e.g., the MEA 100 of FIG. 1). For example, the lower surface of the culture vessel 200 may be attached or coupled to, and detached or uncoupled from, the side/surface of the MEA 100 where the first electrodes 110 are located. Herein, "attached" is not used in the strictest sense, but rather refers to a mechanical contact at the least; mechanical securement may or may not be provided, depending on various construction factors and anticipated usages. If attachment is implemented, any known means may be used, e.g., magnetic or physical attaches.

The culture vessel 200 may transmit (by conductance) an electrical signal generated from the living cells 300 to the first electrodes 110 through the surface attached to the MEA 100. Similarly, the culture vessel 200 may transmit (by conductance) an electrical signal to the living cells 300 from the first electrodes 110 through the surface attached to the MEA 100.

For example, the lower surface (bottom) of the culture vessel 200 may include the conductive material 220. The electrical signal generated from the living cells 300 may be transmitted/conducted to the first electrodes 110 of the MEA 100 through the conductive material 220. The electrical signal transmitted from the first electrodes 110 may be transmitted/conducted to the living cells 300 through the conductive material 220.

The conductive material 220 may be formed through the lower surface (bottom) of the culture vessel 200. The conductive material 220 may be formed in the lower surface (bottom) with a pattern corresponding to a pattern in which the first electrodes 110 of the MEA 100 is formed. The lower surface/bottom of the culture vessel 200 may have through-holes arranged in a pattern to match the pattern of the first electrodes 110. The conductive material 220 may be formed have respective portions formed in the through-holes.

Figure 3:
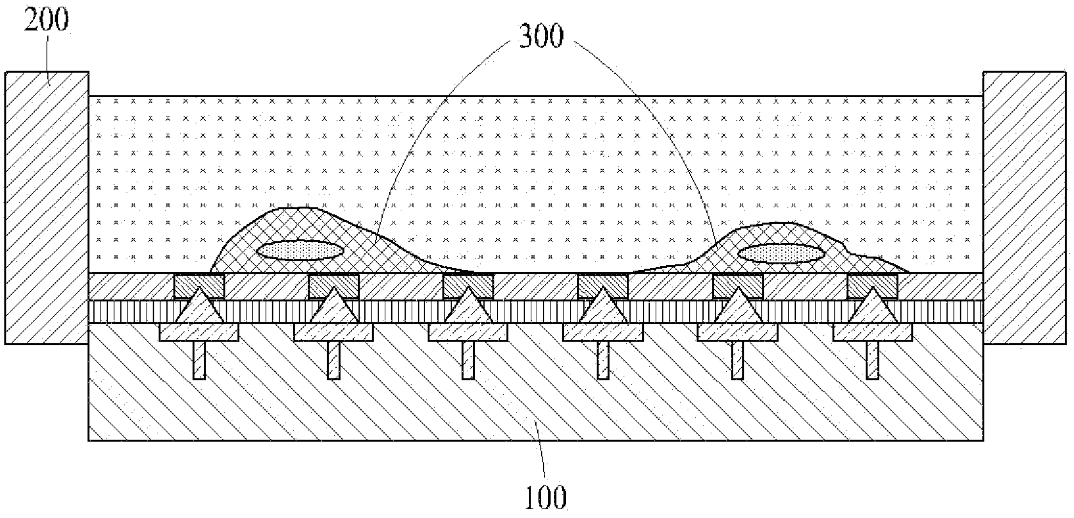
FIG. 3 illustrates an example in which an MEA and a culture vessel are physically and conductively mated, according to one or more embodiments.

FIG. 3 illustrates an example in which the MEA 100 and the culture vessel 200 are physically and conductively mated. The culture vessel 200 illustrated in FIG. 2 is mated or coupled to the MEA 100 illustrated in FIG. 1. As illustrated in FIG. 3, the lower surface (bottom) of the culture vessel 200 may be attached to (or mated with) a side/surface of the MEA 100 having the first electrodes 110. The conductive material 220 on the lower surface of the culture vessel 200 may be physically and/or electrically connected to (mated with) the first electrodes 110 of the MEA 100.

As noted, the through-holes and respectively corresponding portions of the conductive material 220 may be arranged with a pattern corresponding to a pattern of the first electrodes 110, thus allowing a one-to-one mating between the first electrodes 110 and the portions of conductive material 220. In some implementations there may be more through-holes (and portions of conductive material 220) than first electrodes 110, however, each first electrode 110 may mate with a single corresponding portion of the conductive material 220. That is, the conductive material 220 may be formed on the lower surface (bottom) of the culture vessel 200 to correspond to the pattern of the first electrodes 110.

For example, an electrical signal may be generated by electrochemical activity of the living cells 300 and conducted to the first electrodes 110 through the conductive material 220. Similarly, an electrical signal to be induced on the living cells 300 may be input to a device connected to the integrated circuit 120 and conducted through the first electrodes 110 to the living cells 300.

For example, the conductive material 220 may include a metal, a conductive polymer, or any suitable material.

An extended period of time may be needed to culture the living cells 300. The living cells 300 may be cultured in the culture vessel 200 while the culture vessel 200 is separate from the MEA 100 (as illustrated in FIG. 2), for example while the culture vessel 200 is in a controlled environment. In addition, for high throughput production, many culture vessels 200 may be provided with the living cells 300 for culturing. The living cells 300 may be cultured therein while separate from the MEA 100 and in a controlled environment. A culture vessel 200 may be attached to or mated with the MEA 100 to measure the electrical signal generated by the living cells 300 therein. In this way, an electrical signal may be measured from many cases of the living cells 300 using a small number of MEAs 100.

A process of cleaning the MEA 100 device and/or modifying a surface may be used to remove the living cells 300 after an electrical signal has been measured. When the living cells 300 are cultured in the culture vessel 200 that may be attached and detached to and from the MEA 100 and an electrical signal is measured, the process of cleaning the MEA 100 and modifying the surface may not need to be performed, which may reduce the time needed to re-conduct an experiment with the same cultured living cells. In addition, the separability of the culture vessel 200 and the MEA 100 allows the process of cleaning the MEA 100 and/or modifying the surface to be skipped, and thus, damage to the MEA 100 caused by a living cell 300 culture environment may be avoided.

The separability and mate-ability of the culture vessel 200 with respect to the MEA 100 may facilitate measuring an electrical signal from the living cells 300 in various states using a small number of MEAs 100, which may reduce the cost of large-scale applications.

Figure 4:
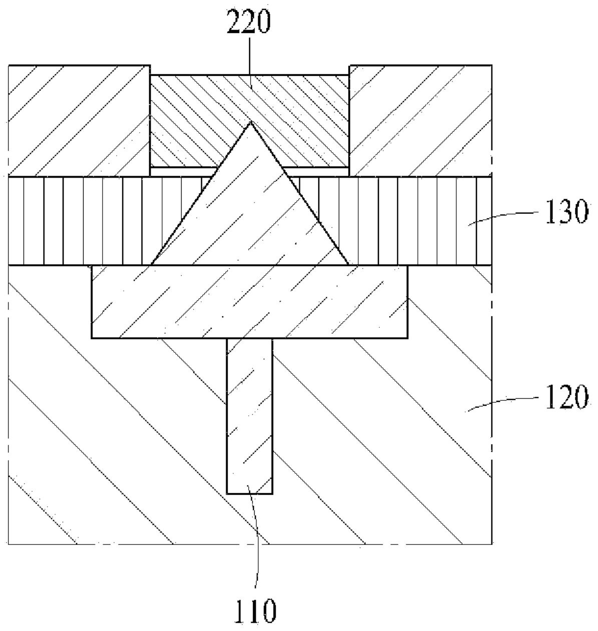
FIG. 4 illustrates an example of a first electrode mated with a conductive material while an MEA and a culture vessel are coupled, according to one or more embodiments.

FIG. 4 illustrates an example of a first electrode 110 mated with (or contacting) the conductive material 220 while the MEA 100 and the culture vessel 200 are coupled. FIG. 4 shows an enlarged portion of FIG. 3, which shows the first electrode 110 and the conductive material 220 connected to each other.

Referring to FIG. 4, in some implementations, the first electrode 110 may be inserted into the conductive material 220 when the culture vessel 200 is attached to the MEA 100 to form a conductive connection ("inserted" refers to deformation, penetration, and/or the like). The first electrode 110 may be formed in a shape such that it may be inserted into the conductive material 220. As illustrated in FIG. 4, the first electrode 110 may be formed in a shape with a pointed end, such as a cone, a triangular pyramid, a pin/needle, or the like. In some embodiments, the first electrode 110 may deform the conductive material 220 due to pressure, and in other embodiments the first electrode 110 may penetrate (e.g., when formed as a needle) the conductive material 220. The conductive material 220 may be pliable or deformable to increase contact area between the conductive material 220 and the first electrode 110.

As illustrated in FIG. 4, the first electrode 110 may be mated with (e.g., inserted or pressed into) the corresponding conductive material 220, and the first electrode 110 and the conductive material 220 may be electrically and physically connected/mated to each other.

Figure 5:
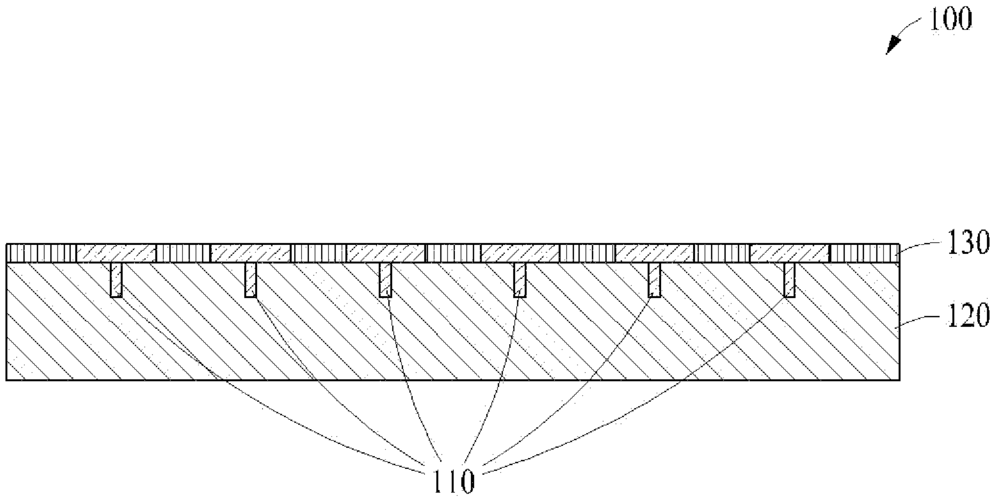
FIG. 5 illustrates another example of an MEA, according to one or more embodiments.

FIG. 5 illustrates another example of the MEA 100. The MEA 100 may include the first electrodes 110, the integrated circuit 120, and the passivation layer 130. The first electrodes 110 may be formed through the passivation layer 130. The first electrodes 110 may include one end (e.g., an upper end) with a flat exterior-exposed surface (e.g., flush or parallel with an upper surface of the passivation layer 130) and another end connected to the integrated circuit 120.

Description of the MEA 100 with reference to FIGS. 1 through 4 is generally applicable to the MEA 100 of FIG. 5.

Figure 6:
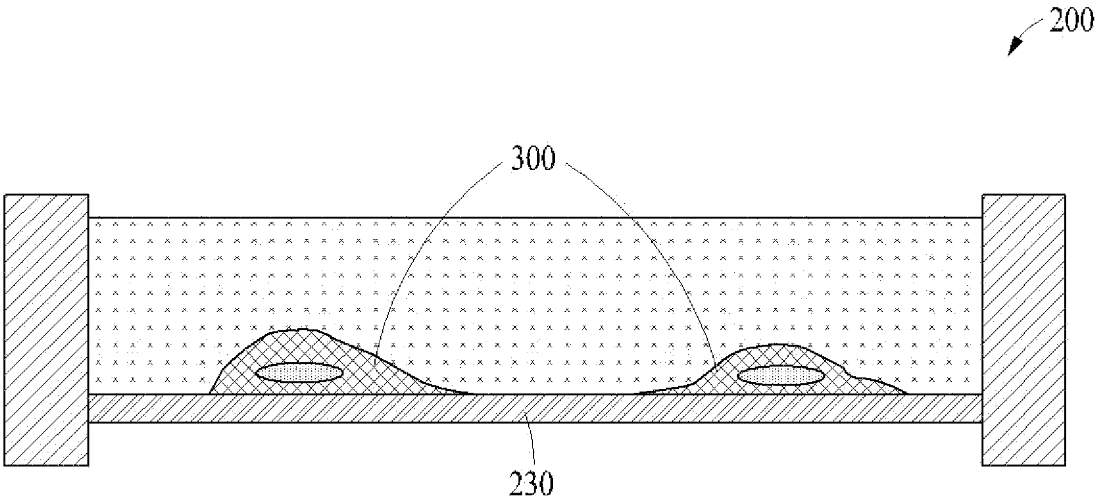
FIG. 6 illustrates an example of a culture vessel including a porous membrane on a bottom of the culture vessel, according to one or more embodiments.

FIG. 6 illustrates an example of the culture vessel 200 including a porous membrane 230 on a bottom of the culture vessel 200. The lower surface (bottom) may include the porous membrane 230 (e.g., a nano-porous membrane). For example, the porous membrane 230 may include a polymer film (e.g., polycarbonate (PC), polyethylene terephthalate (PET), polytetrafluoroethylene (PTFE), polyether sulphone (PES), Silicon Nitride (SiNx), etc.).

As illustrated in FIG. 6, the living cells 300 may be attached or applied to one side (e.g., an upper surface) of the porous membrane 230. The living cells 300 may be attached/applied to the porous membrane 230 and cultured. An electrical signal generated by (or transmitted to) the living cells 300 may be conducted through the porous membrane 230.

Description of the culture vessel 200 with reference to FIGS. 1 through 4 is generally applicable to FIG. 6.

Figure 7:
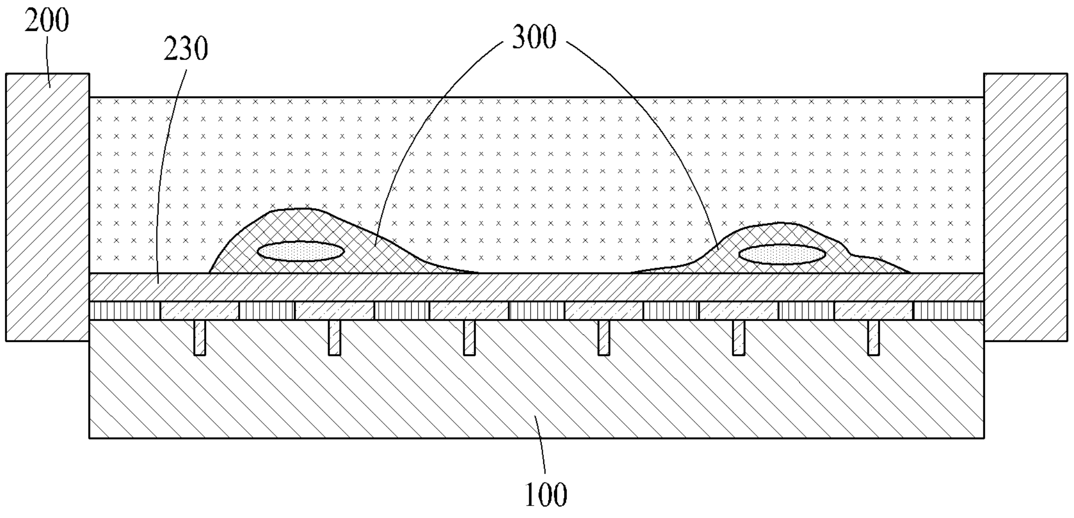
FIG. 7 illustrates an example in which an MEA and a culture vessel are physically and conductively mated, according to one or more embodiments.

FIG. 7 illustrates an example in which the MEA 100 and the culture vessel 200 are mated. Specifically, FIG. 7 illustrates an example the example culture vessel 200 illustrated in FIG. 6 mated to the example MEA 100 illustrated in FIG. 5.

As illustrated in FIG. 7, the culture vessel 200 may be electromechanically attached/mated to, and detached/unmated from, the MEA 100. While the culture vessel 200 is mated to the MEA 100, an electrical signal generated from the living cells 300 may be conductively transmitted to the first electrodes 110 of the MEA 100 through the porous membrane 230. Similarly, while the culture vessel 200 is mated to the MEA 100, an electrical signal may be conductively transmitted from the first electrodes 110 through the porous membrane 230 to the living cells 300.

Figure 8:
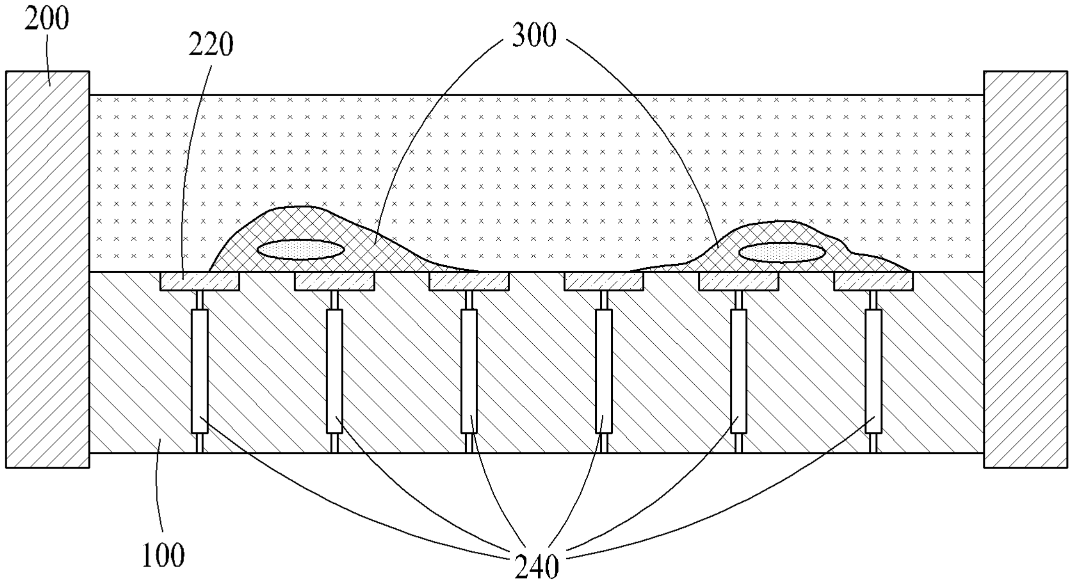
FIG. 8 illustrates an example of a culture vessel including second electrodes, according to one or more embodiments.

FIG. 8 illustrates an example of the culture vessel 200 including second electrodes 240. The culture vessel 200 may include the second electrodes 240 vertically (e.g., in a vertical direction of FIG. 8) penetrating a surface attached to the MEA 100. For example, a lower surface attached to the MEA 100 may include the second electrodes 240 vertically penetrating the lower surface/bottom of the culture vessel 200.

For example, the lower surface/bottom illustrated in FIG. 8 may include a through-silicon-via (TSV) electrode structure. The second electrodes 240 may have conductive material 220 formed on an end (e.g., in a 12 o'clock position as illustrated in FIG. 8) exposed to the living cells 300 and may include a pogo pin penetrating the lower surface from each of the portions of conductive material 220 of the respective second electrodes 240. A portion of the pogo pin may protrude toward/from a side (e.g., in a 6 o'clock position as illustrated in FIG. 8) in which the lower surface is attached to the MEA 100. A pogo pin may protrude from a lower surface of the bottom of the culture vessel 200, for example in a default extended position provided by a spring element and may be pushed in/up when the culture vessel 200 mates with the MEA 100.

Descriptions of the culture vessel 200 with reference to FIGS. 1 through 4 may generally apply to FIG. 8 in the same general manner.

Figure 9:
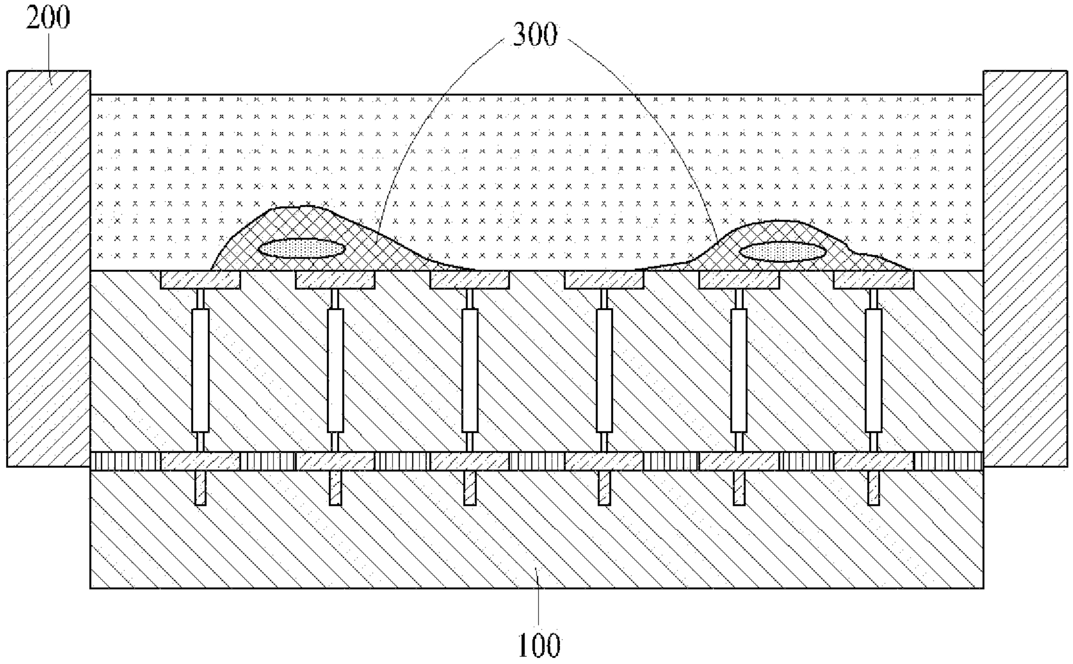
FIG. 9 illustrates an example in which an MEA and a culture vessel are physically and conductively mated, according to one or more embodiments.

FIG. 9 illustrates an example in which the MEA 100 and the culture vessel 200 are mated. FIG. 9 illustrates an example in which the culture vessel 200 illustrated in FIG. 8 is mated with the MEA 100 illustrated in FIG. 5.

As illustrated in FIG. 9, the culture vessel 200 may be electromechanically attached/mated to, and detached/unmated from, the MEA 100. While the culture vessel 200 is mated with to the MEA 100, an electrical signal generated from the living cells 300 may be conductively transmitted through the second electrodes 240 to the first electrodes 110 of the MEA. While the culture vessel 200 is attached to or mated with the MEA 100, an electrical signal transmitted from the first electrodes 110 may be transmitted to the living cells 300 through the second electrodes 240.

Figure 10:
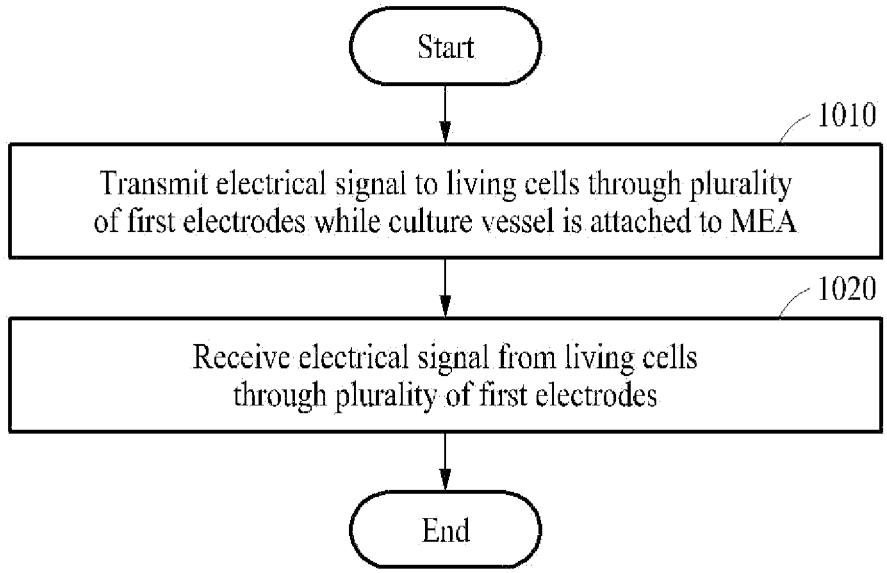
FIG. 10 illustrates an example of a measurement method using an MEA and a culture vessel, according to one or more embodiments.

FIG. 10 illustrates an example of a measurement method using any of examples of the MEA 100 and the culture vessel 200. In operation 1010, the MEA 100 having the culture vessel 200 attached/mated thereto may transmit an electrical signal to the living cells 300 through the first electrodes 110. For example, the living cells 300 may be in a cultured state by being attached/applied to one side of a lower surface (bottom) of the culture vessel 200. Liquid culturing media (nutrients, etc.) may also be contained in the culture vessel 200.

For example, the electrical signal may be transmitted to the living cells 300 through the lower surface of the culture vessel 200 by the first electrodes 110. For example, the lower surface of the culture vessel 200 may include at least one of the conductive material 220, the porous membrane 230, and/or the second electrodes 240, or any combination thereof.

In operation 1020, the MEA 100 may receive an electrical signal from the living cells 300 through the first electrodes 110. For example, the electrical signal may be generated by the living cells 300 through an electrochemical reaction (e.g., nerve activity). The electrical signal may be conductively transmitted to the first electrodes 110 which penetrate the lower surface (bottom) of the culture vessel 200.

The integrated circuit 120 of the MEA 100 may receive the electrical signal generated by the living cells 300 via the first electrodes 110. The integrated circuit 120 may amplify the electrical cell signal and transmit the amplified electrical cell signal to a device for signal processing; the device is connected to the integrated circuit 120 by any of various wired or wireless communication channels. For example, the integrated circuit 120 may include a MUX and transmit the electrical signal received via some and/or all of the first electrodes 110 to an external device. That is, when there are too many first electrodes 110 to concurrently transmit all of their respective signals to the external device at the same time, the MUX may be used to transmit signals of subsets of the first electrodes device 110 at different cycles. The integrated circuit 120 may include an amplifier and amplify the electrical signals received by the first electrodes 110.

Figure 11:
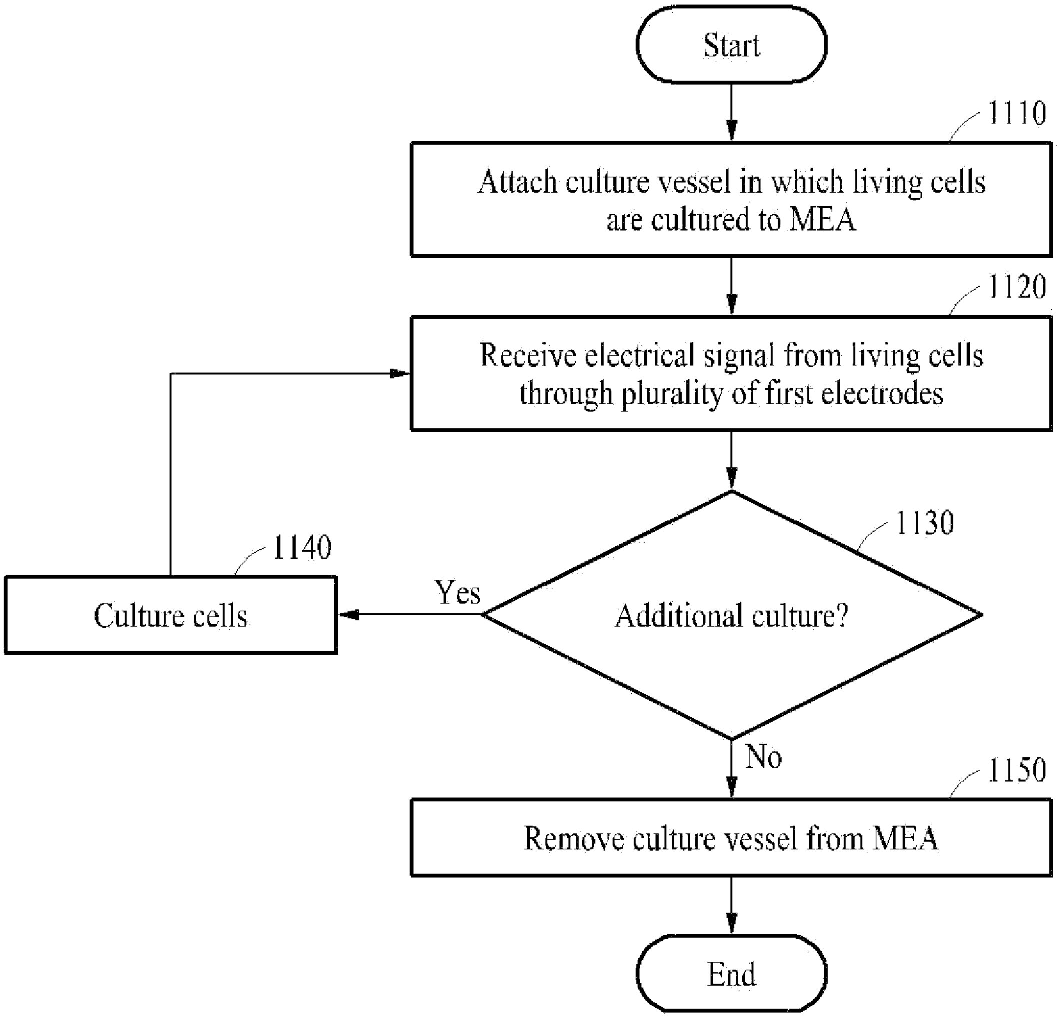
FIG. 11 illustrates an example of a measurement method using an MEA and a culture vessel, according to one or more embodiments.

FIG. 11 illustrates an example of a measurement method using any of the examples or embodiments of the MEA 100 and the culture vessel 200. In operation 1110, the culture vessel 200 in which the living cells 300 are cultured may be attached/applied to the MEA 100. The living cells 300 may be cultured while the culture vessel 200 is separate from the MEA 100, i.e., is not mated with the MEA 100. The culture vessel 200 may be in a controlled environment, depending on any needs of the living cells 300.

In operation 1120, the MEA 100 may receive an electrical signal from the living cells 300 through the first electrodes 110. For example, the electrical signal may be conductively transmitted to the first electrodes 110 from the living cells 300 by penetrating a lower surface (bottom) of the culture vessel 200.

The lower surface/bottom may include the conductive material 220 (e.g., with portions in respective through-holes of the lower surface/bottom), the porous membrane 230, or the second electrodes 240, or any combination thereof. The electrical signal generated from the living cells 300 may be conductively transmitted via the first electrodes 110 through at least one of the conductive material 220, the porous membrane 230, or the second electrodes 240, or any combination thereof.

In operation 1130, a determination may be made of whether additional culturing of the living cells 300 is needed. For example, an MEA system may make the determination. A device (e.g., a processor) for analyzing an electrical signal that is connected to the MEA 100 may make the determination of whether the additional culturing is needed.

When the electrical signal of the living cells 300 is sufficiently strong (e.g., above a threshold power level or signal-to-noise level), the device may determine that additional culturing of the living cells 300 is needed, for example to observe change in the living cells 300 over time.

When the electrical signal is sufficiently weak (e.g., below the threshold) and therefore, for example, unsuitable for identifying and connection relationships between cells and/or for deriving information about connection strength between the living cells 300, the device may determine that the living cells 300 are unviable and are to be discarded.

In some examples, when the electrical cell signal is weak and unsuitable for deriving information about connection relationships and/or connection strength between the living cells 300, the device may determine that the additional culturing of the living cells 300 is needed. A criterion for determining whether the additional culture is needed is not limited to the above-described examples.

In response to a determination of operation 1130 that additional culturing of the living cells 300 is needed, the living cells 300 may be cultured in operation 1140. For example, while the culture vessel 200 is separate/unmated from the MEA 100, the living cells 300 may be cultured, for example in a controlled environment.

In response to a determination of operation 1130 that additional culturing of the living cells 300 is not needed, the culture vessel 200 may be removed from the MEA 100 in operation 1150. For example, the removed culture vessel 200 (or its contents) may be discarded.

Operations 1110 through 1150 may be performed by an MEA system. For example, the MEA system may include the culture vessel 200, the MEA 100, the device for analyzing an electrical signal, and/or a device for attaching/mating and detaching/unmating the culture vessel 200 to and from the MEA 100, or any combination thereof. In some embodiments, a robot may perform the detaching/unmating and the attaching/mating according to control signals from the MEA system.

The device (e.g., robot) for attaching/mating and detaching/unmating the culture vessel 200 to and from the MEA 100 may attach or couple the culture vessel 200 to the MEA 100 in operation 1120 or may remove the culture vessel 200 from the MEA 100 in operation 1140 and/or operation 1150.

When coupling the culture vessel 200 to the MEA 100, the device for attaching and detaching may cause the conductive material 220 on a lower surface (bottom) of the culture vessel 200 to be correspondingly electrically connected to the first electrodes 110 of the MEA 100.

In addition to the device for attaching and detaching the culture vessel 200 to and from the MEA 100, various ways may be used to attach/mate and detach/de-mate the culture vessel 200 to and from the MEA 100. An external device (e.g., the device for processing an electrical signal and/or the device for attaching and detaching the culture vessel 200 to and from the MEA 100) may determine whether the conductive material 220 on the lower surface of the culture vessel 200 and/or the second electrodes 240 are correspondingly connected to the first electrodes 110 of the MEA 100.

The device for analyzing an electrical signal may determine whether the first electrodes 110 of the MEA 100 are correspondingly connected to the conductive material 220 on the lower surface (bottom) of the culture vessel 200 and/or the second electrodes 240 by transmitting a test signal through the MEA 100. The device for analyzing an electrical signal may adjust a position at which the culture vessel 200 is attached to the MEA 100 by transmitting a control signal to the device for reattaching the culture vessel 200 to the MEA 100.

The operations illustrated in FIGS. 10 and 11 may be performed using any of the culture vessels 200 or the MEAs 100 of FIGS. 1 through 9, or any combination thereof. The descriptions of the culture vessel 200, the MEA 100, and the device for analyzing an electrical signal referring to FIGS. 1 through 9 generally apply to FIGS. 10 and 11 in the same general manner.

Some of the operations illustrated in FIGS. 10 and 11 may be omitted or performed in a different order. For example, the electrical signal may be measured from the living cells 300 by performing operations 1010 and 1020 in a different order in FIG. 10.

The computing apparatuses, the signal processing devices, the electronic devices, the processors, the memories, the information output system and hardware, the storage devices, and other apparatuses, devices, units, modules, and components described herein with respect to FIGS. 1-11 are implemented by or representative of hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-11 that perform the operations described in this application are performed by computing hardware, for example, by one or more processors or computers, implemented as described above implementing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions herein, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents.

Therefore, in addition to the above disclosure, the scope of the disclosure may also be defined by the claims and their equivalents, and all variations within the scope of the claims and their equivalents are to be construed as being included in the disclosure.

What is claimed is:

1. A device comprising:

a culture vessel in which living cell material is cultured, the culture vessel comprising a planar bottom wall comprising through-holes having an arrangement pattern and each filled with a portion of deformable conductive material; and a multi-electrode array (MEA) comprising a planar surface projecting from which are first electrodes having the arrangement pattern and each configured to conductively receive an electrical signal generated by the living cell material and conductively transmit an electrical signal to the living cell material through the first electrodes, wherein the culture vessel is detachably mateable with the MEA, and is configured to, when mated with the MEA, conductively transmit an electrical signal generated by the living cell to the first electrodes or conductively transmit an electrical signal to the living cell via the first electrodes through a surface mated with the MEA, and wherein the MEA and the culture vessel are configured such that when they are mated the first electrodes projecting from the planar surface contact and deform the portions of deformable conductive material in the respectively corresponding through-holes.

2. The device of claim 1, wherein the first electrodes are configured such that when the MEA is mated with the culture vessel the first electrodes penetrate the respective portions of the conductive material.

3. The device of claim 2, wherein the first electrodes being inserted into the portions of the conductive material comprise respective ends of the first electrodes deforming or penetrating the portions of the deformable conductive material.

4. The device of claim 1, wherein the culture vessel comprises a porous membrane layered an upper surface of the planar bottom wall.

5. The device of claim 1, wherein the culture vessel comprises second electrodes vertically penetrating the bottom and arranged with the pattern.

6. The device of claim 1, wherein the MEA comprises:

an integrated circuit; and a passivation layer formed on one side of the integrated circuit, and wherein the first electrodes are connected to the integrated circuit through the passivation layer.

7. The device of claim 1, wherein each portion of deformable conductive material has an upper surface that is coplanar with an upper surface of the planar bottom wall of the culture vessel, the upper surfaces of the portions of deformable conductive material and the upper surface of the planar bottom wall form a bottom surface of the culture vessel, and wherein each portion of the deformable conductive material has a lower surface that is deformed by contact with a respectively corresponding first electrode.

* * * * *